United States Patent
Dacosta et al.

(10) Patent No.: US 10,456,182 B2
(45) Date of Patent: Oct. 29, 2019

(54) FORCE DISTRIBUTION IMPLANT, ASSEMBLY AND KIT

(71) Applicant: PARAGON 28, INC., Englewood, CA (US)

(72) Inventors: Albert Dacosta, Lone Tree, CO (US); Frank Bono, Castle Rock, CO (US); Joshua L. Haddix, Lakewood, OH (US)

(73) Assignee: PARAGON 28, INC., Englewood, CO (US)

( * ) Notice: Subject to any disclaimer, the term of this patent is extended or adjusted under 35 U.S.C. 154(b) by 849 days.

(21) Appl. No.: 14/776,149

(22) PCT Filed: Mar. 13, 2013

(86) PCT No.: PCT/US2013/030768
§ 371 (c)(1),
(2) Date: Sep. 14, 2015

(87) PCT Pub. No.: WO2014/142823
PCT Pub. Date: Sep. 18, 2014

(65) Prior Publication Data
US 2016/0030098 A1 Feb. 4, 2016

(51) Int. Cl.
*A61B 17/86* (2006.01)

(52) U.S. Cl.
CPC ...... *A61B 17/8695* (2013.01); *A61B 17/8605* (2013.01)

(58) Field of Classification Search
CPC ................. A61B 17/8605; A61B 17/8695
USPC .......................... 606/302, 303, 322
See application file for complete search history.

(56) References Cited

U.S. PATENT DOCUMENTS

| 9,198,769 | B2* | 12/2015 | Perrow | A61B 17/8042 |
| 9,522,024 | B2* | 12/2016 | Ziolo | A61B 17/8605 |
| 2001/0031966 | A1 | 10/2001 | Tormala et al. | |
| 2002/0133158 | A1 | 9/2002 | Saint Martin | |
| 2004/0106925 | A1 | 6/2004 | Culbert | |
| 2007/0233125 | A1 | 10/2007 | Wahl et al. | |
| 2008/0177330 | A1 | 7/2008 | Ralph et al. | |

(Continued)

OTHER PUBLICATIONS

Extended European Search Report issued by the European Patent Office for European Patent Application No. 13878311.3 dated Oct. 10, 2016.

(Continued)

*Primary Examiner* — Anu Ramana
(74) *Attorney, Agent, or Firm* — Heslin Rothenberg Farley & Mesiti P.C.

(57) ABSTRACT

An implant for use with a bone screw for fixation of at least one bone or bone fragments. The implant includes a top end and a bottom end. The implant may also include an exterior surface extending from the top end to the bottom end and a central bore extending from the top end to the bottom end along a central axis. The implant may further include a slot extending through the exterior surface and intersecting with the central bore of the implant. A bone fixation assembly including a fixator and an implant configured to engage the fixator is also disclosed. A surgical kit for bone fixation is also disclosed. The surgical kit includes at least one force distribution member and at least one elongate member.

18 Claims, 13 Drawing Sheets

(56) References Cited

U.S. PATENT DOCUMENTS

2008/0306555 A1    12/2008   Patterson et al.
2013/0035724 A1     2/2013   Fitzpatrick

OTHER PUBLICATIONS

International Search Report for PCT/US2013/030768 dated Dec. 9, 2013.
Sep. 15, 2015: International Report on Patentability for International Application No. PCT/US2013/030768.

* cited by examiner

FORCE DISTRIBUTION IMPLANT, ASSEMBLY AND KIT

CROSS REFERENCE TO RELATED APPLICATIONS

This application is a national stage filing under section 371 of International Application No. PCT/US2013/030768 filed on Mar. 13, 2013, and published in English on Sep. 18, 2014 as WO 2014/142823 A1, which is incorporated herein by reference in its entirety.

FIELD OF THE INVENTION

The present invention relates generally to a force distribution member for use with a bone fastener. More specifically, but not exclusively, the present invention concerns an implant for use with a bone fastener to distribute loads and enhance fastener fixation.

SUMMARY OF THE INVENTION

Aspects of the present invention provide an implant for use with a bone fastener, for example, a bone screw for fixation.

In one aspect, provided herein is an implant including a top end and a bottom end. The implant may also include an exterior surface extending from the top end to the bottom end. The implant may further include a central bore extending from the top end to the bottom end along a central axis. The implant may also include a slot extending through the exterior surface and intersecting with the central bore of the implant.

In another aspect, provided herein is a bone fixation assembly. The bone fixation assembly including a fixator and an implant configured to engage the fixator. The implant may include a top end and a bottom end. The implant may also include an exterior surface and internal surface extending from the top end to the bottom end and an internal bore extending from the top end to the bottom end along a central axis. The implant may further include an opening extending through the exterior surface and internal surface of the implant.

In yet another aspect, provided herein is a surgical kit for bone fixation. The surgical kit may include at least one force distribution member and at least one elongate member. The force distribution member may include a top end and a bottom end. The force distribution member may also include an outer surface extending from the top end to the bottom end and a channel extending from the top end to the bottom end along a central axis. The force distribution member may further include an aperture extending through the outer surface and into the channel of the implant.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Figure 1:
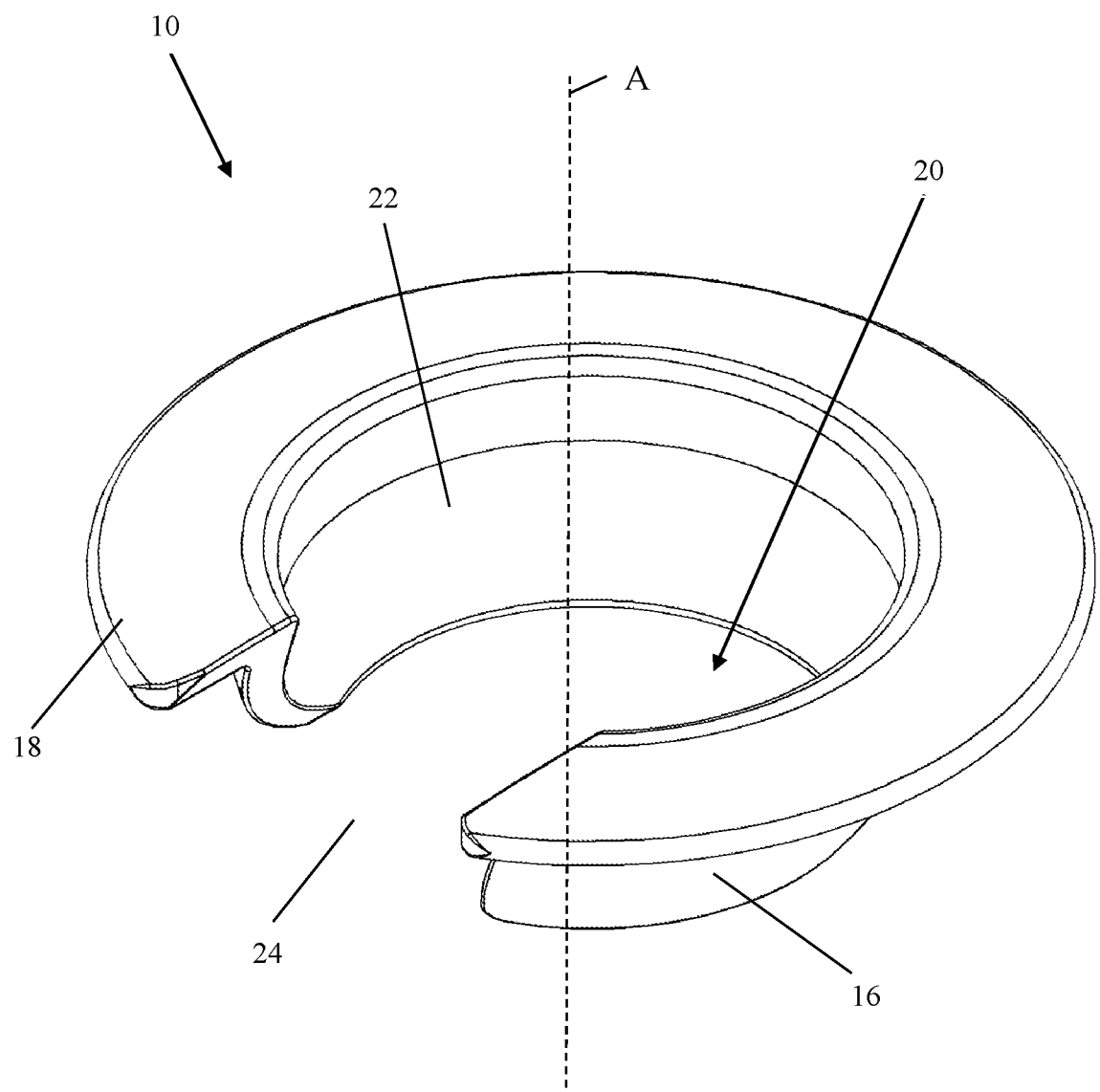
FIG. 1 is a perspective view of an implant, in accordance with an aspect of the present invention.

Generally stated, disclosed herein are implants for improved bone fixation. As used herein, the terms "force distribution member," "washer implant," "washer," "split washer," and "implant" may be used interchangeably as they essentially describe the same type of device. Further, a surgical method for inserting the implants onto a fastener to increase fixation in compromised bones is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means a direction towards the midline of the body, "lateral" is a direction towards the sides or away from the midline of the body, "superior" means a direction above and "inferior" means a direction below another object or structure.

Referring to the drawings, wherein like reference numerals are used to indicate like or analogous components throughout the several views, and with particular reference to FIGS. 1-5, there is illustrated an exemplary embodiment implant 10. The implant 10 may include a top end 12 and a bottom end 14. An exterior or outer surface 16 of the implant 10 may extend from the top end 12 to the bottom end 14. The implant 10 may also include a rim or extension 18 extending radially out from the exterior surface 16 at the top end 12 of the implant 10. The rim 18 may extend at least partially around the implant 10. A central bore 20 may extend from the top end 12 to the bottom end 14 along a central axis A of the implant 10. The central bore 20 is defined by an interior or inner surface 22 of the implant 10. The implant 10 may also include a slot 24 extending through the exterior surface 16, the interior surface 22 and into the central bore 20. The terms "central bore," "internal bore" and "through hole" may be used interchangeably herein as they essentially describe the same type of feature.

Figure 2:
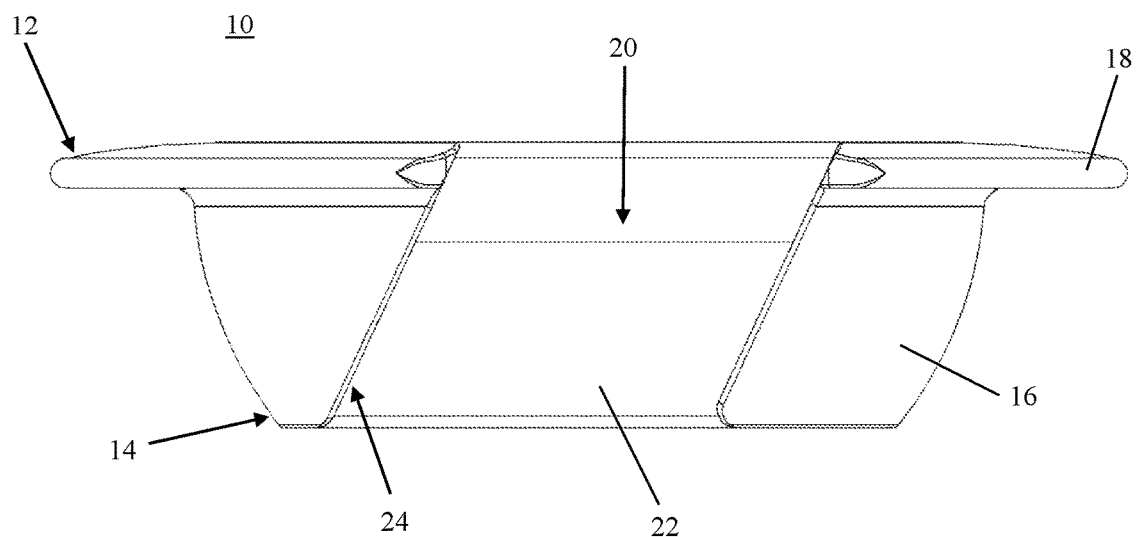
FIG. 2 is a side view of the implant of FIG. 1, in accordance with an aspect of the present invention.
Figure 3:
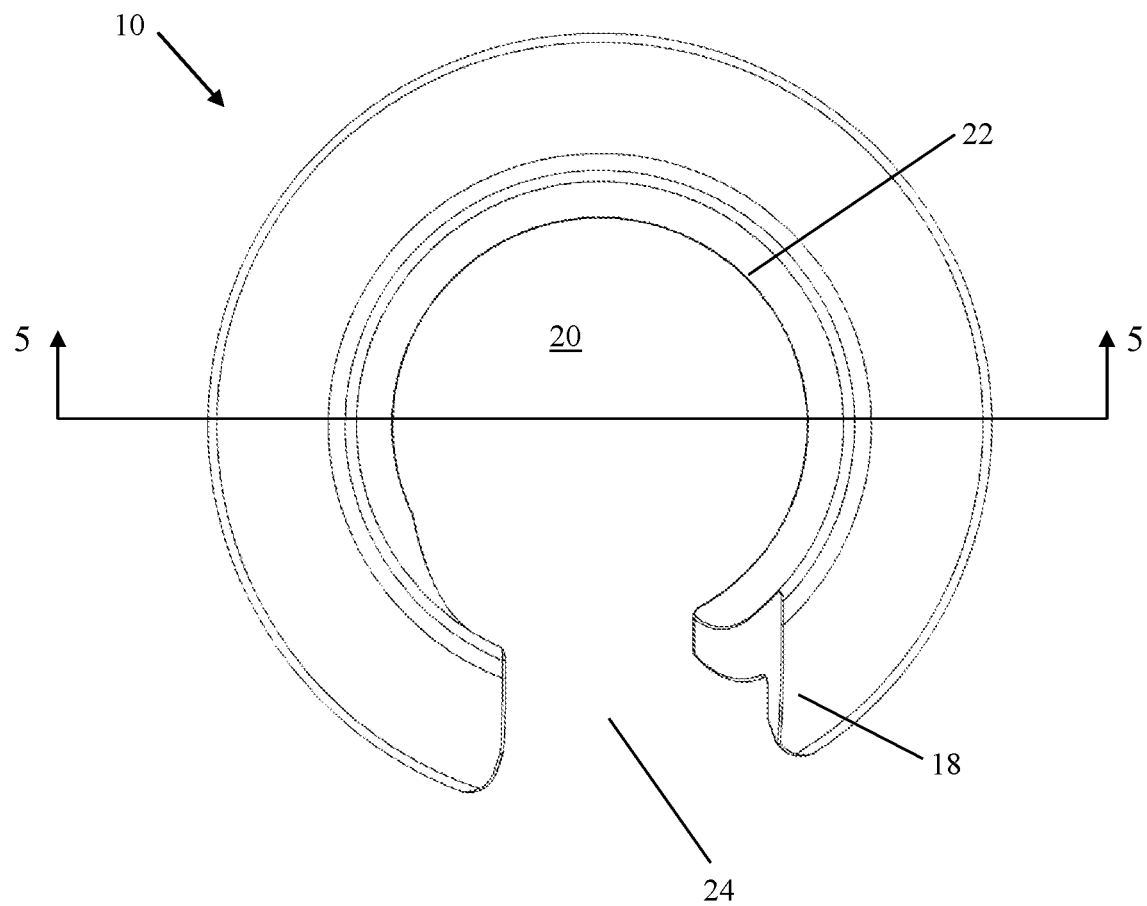
FIG. 3 is a top view of the implant of FIG. 1, in accordance with an aspect of the present invention.
Figure 4:
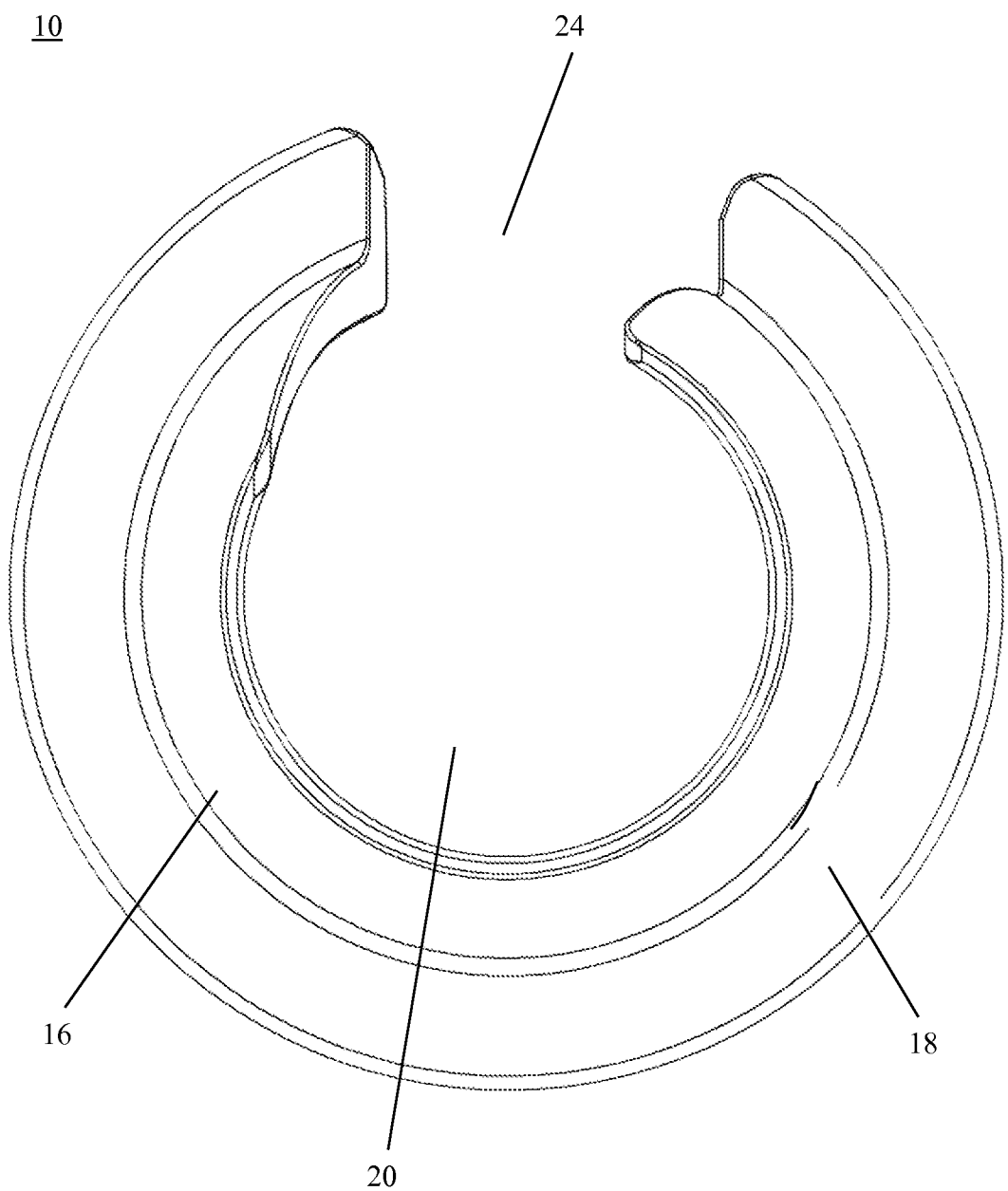
FIG. 4 is a bottom view of the implant of FIG. 1, in accordance with an aspect of the present invention.
Figure 5:
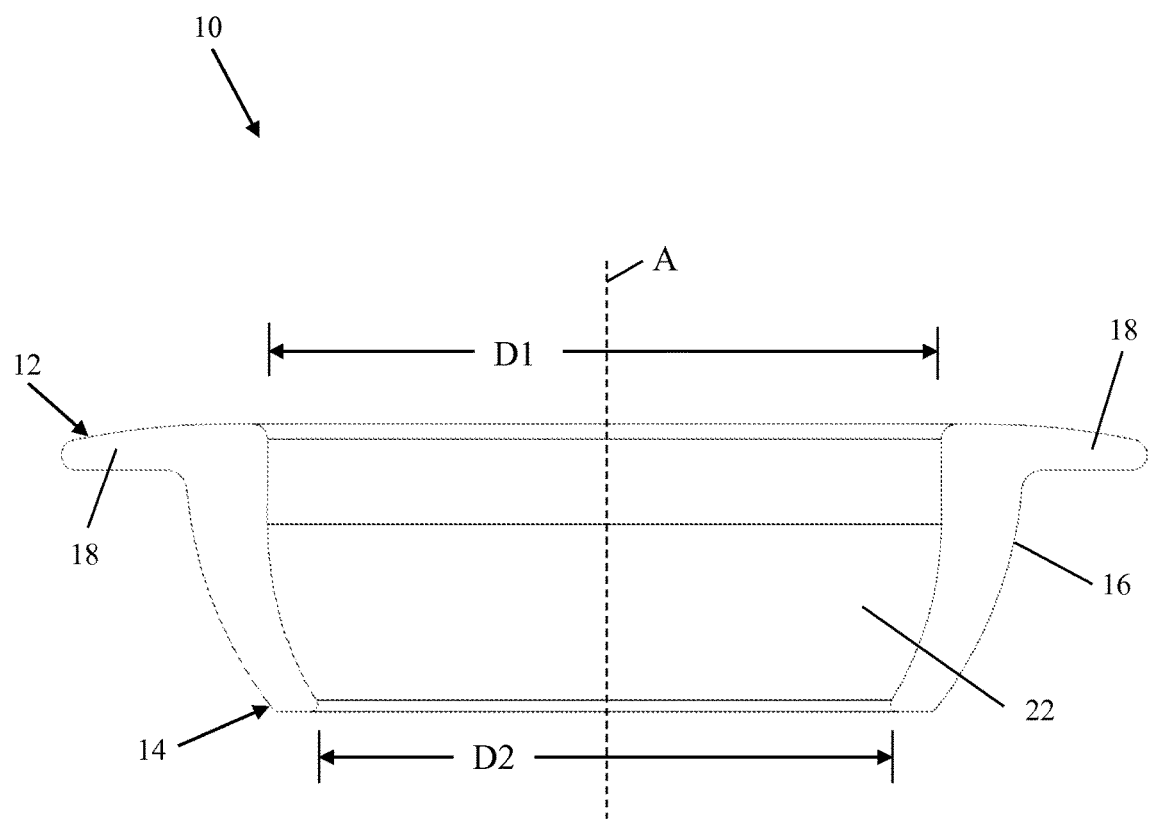
FIG. 5 is a cross-sectional view of the implant shown in FIG. 3 as viewed along section line 5-5, in accordance with an aspect of the present invention.

As shown in FIG. 2, the exterior surface 16 may be curved from the top end 12 to the bottom end 14. The exterior surface 16 is curved to allow for better load distribution between the head of a fastener, for example, a bone screw 30, and the bone contacting the exterior surface 16. Alternative fasteners may include olive wires, pins, fixation members, and the like. The exterior surface 16 of the implant 10 may also be tapered from the top end 12 to the bottom end 14. The central bore 20 may be configured to engage the head of a fastener, for example, the bone screw 30. The terms "fastener," "fixator," "elongate member," "bone screw," and "screw" may be used interchangeably herein as they essentially describe the same type of device. The implant 10, for example purposes is shown to have a generally round or oval external geometry, however other geometric configurations may be used. The top end 12 of the implant 10 may have a first inner diameter D1 and the bottom end 14 of the implant 10 may have a second inner diameter D2. The first inner diameter D1 may be larger than the second inner diameter D2. The interior surface 22 may be concavely curved or arcuate from the top end 12 to the bottom end 14. The arcuate configuration of the inner surface 22 allows for pivoting of a fastener as well as allowing for better load distribution and surface contact.

The rim 18 of the implant 10 may be configured to engage a surface, for example, a bone surface. The rim 18 may be configured to increase the surface area in contact with the surface to allow for increased force distribution. The rim 18 and exterior surface 16 of the implant 10 may provide more surface area for contact with the surface than the screw alone. In addition, the central bore 20 may be configured to engage a shaft of a screw, for example, a bone screw 30 which may include a tapered shaft, described in greater detail below, which has already been partially inserted into a patient's bone or prior to insertion into the patient's bone.

Figure 10:
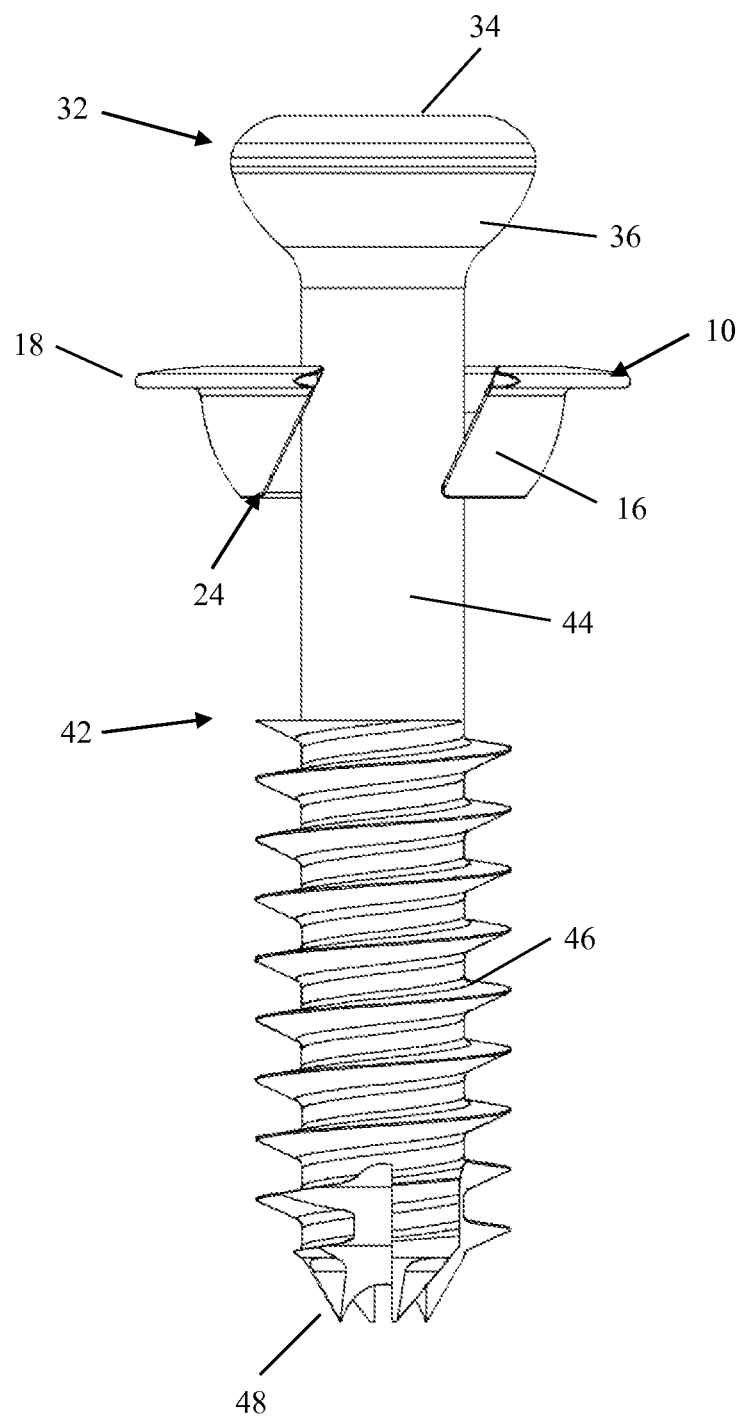
FIG. 10 is a front view of the implant of FIG. 1 with a screw being inserted, in accordance with an aspect of the present invention.

As shown in FIG. 10, the slot or opening 24 may be configured to allow the implant 10 to be inserted onto a screw from a side of the screw which has already been partially inserted into a surface. The slot 24 may extend through the exterior surface 16, the interior surface 22 and into the central bore 20. The slot 24 may also extend through the rim 18. The slot 24 of the implant 10 may be angled from the top end 12 to the bottom end 14, as shown in FIG. 2. The slot 24 may be angled, for example, between approximately 15 to 40 degrees relative to the central axis A of the implant 10, more preferably approximately 20 to 30 degrees, and most preferable may be approximately 25 degrees. In addition, the slot 24 may be offset from the central axis A, for example, the slot 24 may be offset between approximately 0.3 mm and 1.6 mm. The slot 24 for a 7 mm implant 10 may be offset between, for example, approximately 0.4 mm and 1.2 mm, and more preferably approximately 0.8 mm. The slot 24 is configured to lock the implant 10 to the fastener 30 and prevent the implant 10 from being forced off of the fastener 30 during insertion into a patient's bones.

Figure 11:
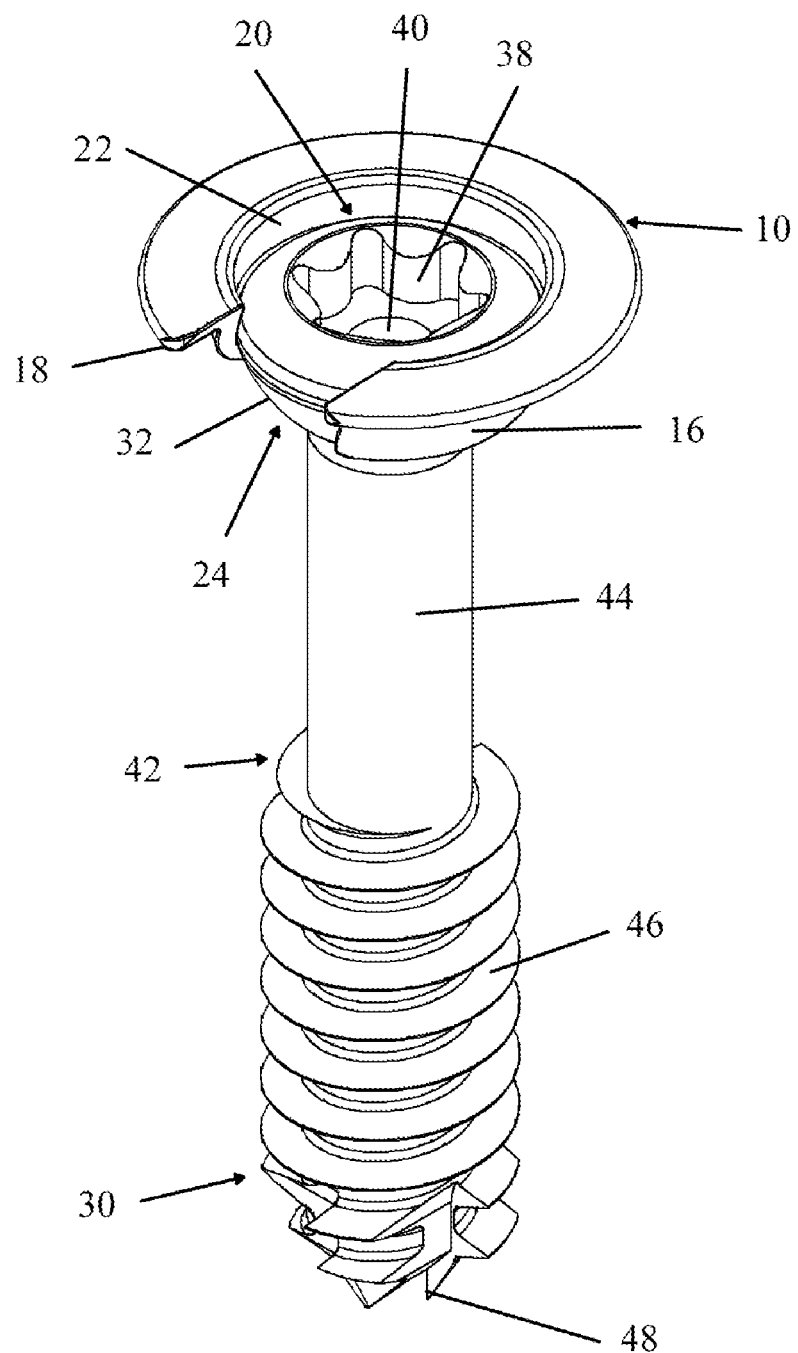
FIG. 11 is a perspective view of the implant of FIG. 1 engaging the head of the screw, in accordance with an aspect of the present invention.
Figure 12:
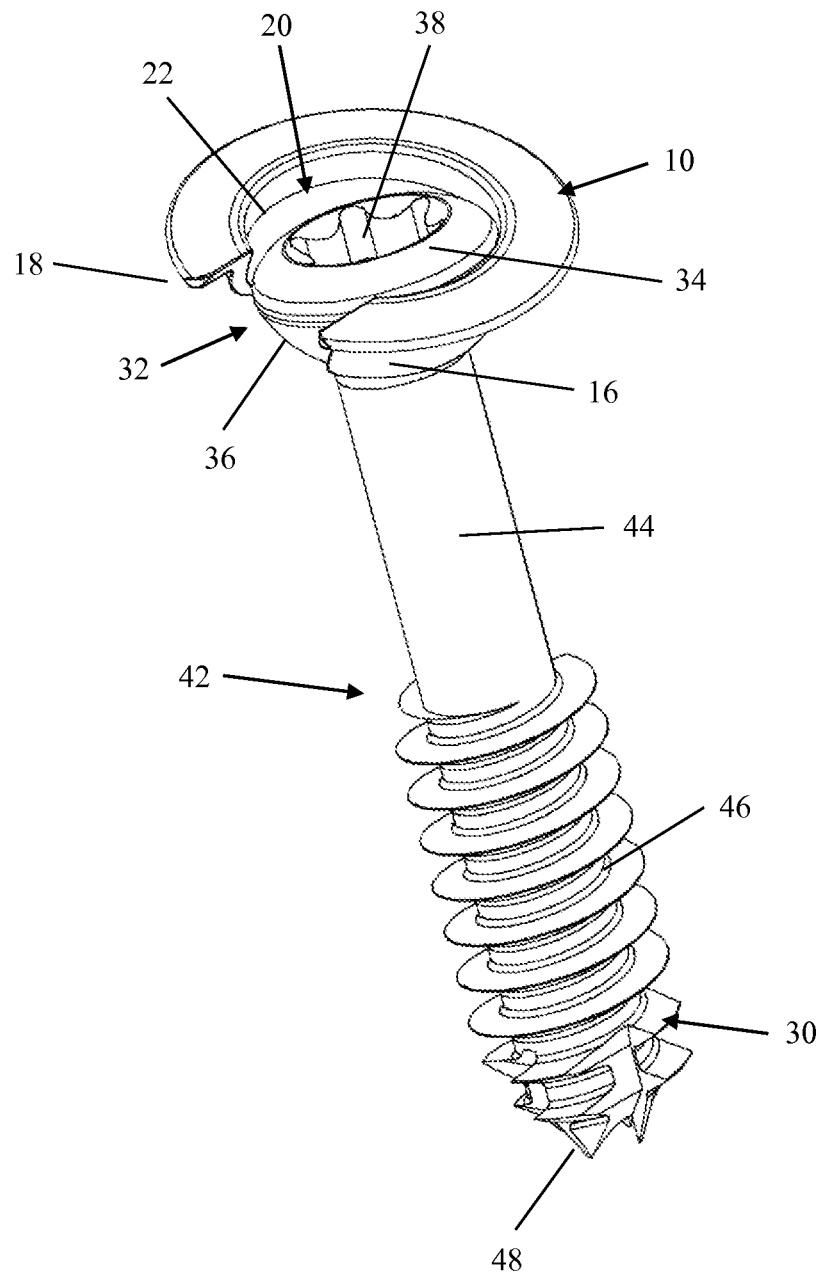
FIG. 12 is a perspective view of the implant of FIG. 1 engaging the head of the screw of FIG. 9 in an angled position, in accordance with an aspect of the present invention.

As shown in FIGS. 11 and 12, the implant 10 may be used with a screw, for example, a bone screw 30, to increase the surface area for load distribution. Bone screw fixation is difficult to achieve and maintain in bones with compromised material strength, for example bones with osteoporosis or advanced osteopenia. The implant 10 provides additional surface area for contacting the bones being fixed. In addition, the implant 10 may be inserted onto the screw 30 without removing and re-installing an already implanted screw 30. Since the implant 10 does not require removal and re-installation of implanted screw 30 further damage to already compromised bones is prevented.

Figure 14:
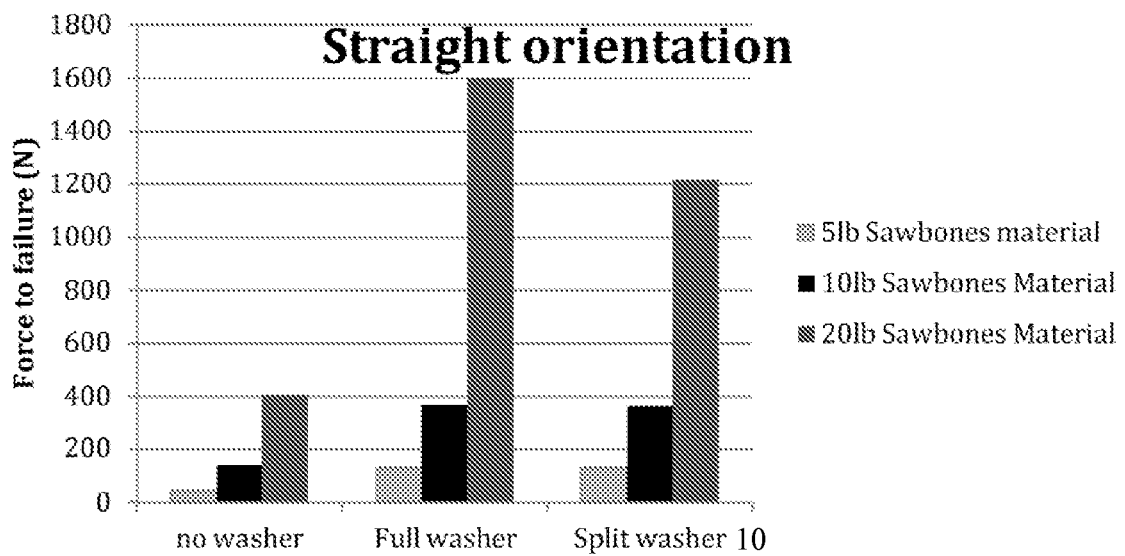
FIG. 14 depicts a graph showing axial pull through force to failure test results, in accordance with an aspect of the present invention.

FIG. 14 shows a bar graph of the measured axial pull through force to failure test results comparing the force to failure of a bone screw 30 (Monster Screw System™, Paragon 28, Inc., Englewood, Colo.) with no washer, a full washer, and the implant 10 described herein. The force to failure tests were conducted using solid rigid polyurethane foam test material (e.g., Sawbones, Pacific Research Laboratories, Inc., Vashon, Wash.) with densities of 5 pcf, 10 pcf, and 20 pcf. The implant 10 was a 7.0 mm implant and the full washer or non-split washer was a 7 mm screw washer. The force to failure tests were conducted by inserting the bone screws 30 with or without a washer or implant 10 through the foam test samples and loading the screws in tension along the axis of the screw until failure occurred using an Instron 8821s bi-axial servo-hydraulic load frame. The tests were conducted by inserting the screws with and without the washers or implants 10 in various off-axis screw orientations into the foam material on a flat surface of the foam test samples, so the inferior shaft of the screws extended out of the foam material. The force to failure tests were then conducted by loading the screws in tension along the axis of the screw until failure occurred using an Instron 8821s bi-axial servo-hydraulic load frame and the failure forces were recorded.

As shown in FIG. 14, in the 5 pcf foam material, the screws with washers or implants 10 demonstrated similar force to failure and the screws with washers or implants 10 demonstrated higher forces to failure than the screws without washers or implants 10. Also depicted in FIG. 14, the screws with the full washer and implant 10, in the 10 pcf foam material, showed nearly similar force to failure and all the screws with washers or implants 10 showed significantly higher force to failure than the screws without washers or implants 10. The screws with implants 10 exhibited lower force to failure than the screw with the full washer and all the screws with washers or implants 10 exhibited higher force to failure than the screws without washers or implants 10, in the 20 pcf foam material, as seen in FIG. 14.

The present invention also discloses a kit including at least two implants 10 for use with a screw, for example, bone screw 30, in a surgical procedure. The kit may further include at least one screw 30. The kit may also include a variety of tools for inserting an implant 10, as well as for inserting the screw 30.

Figure 6:
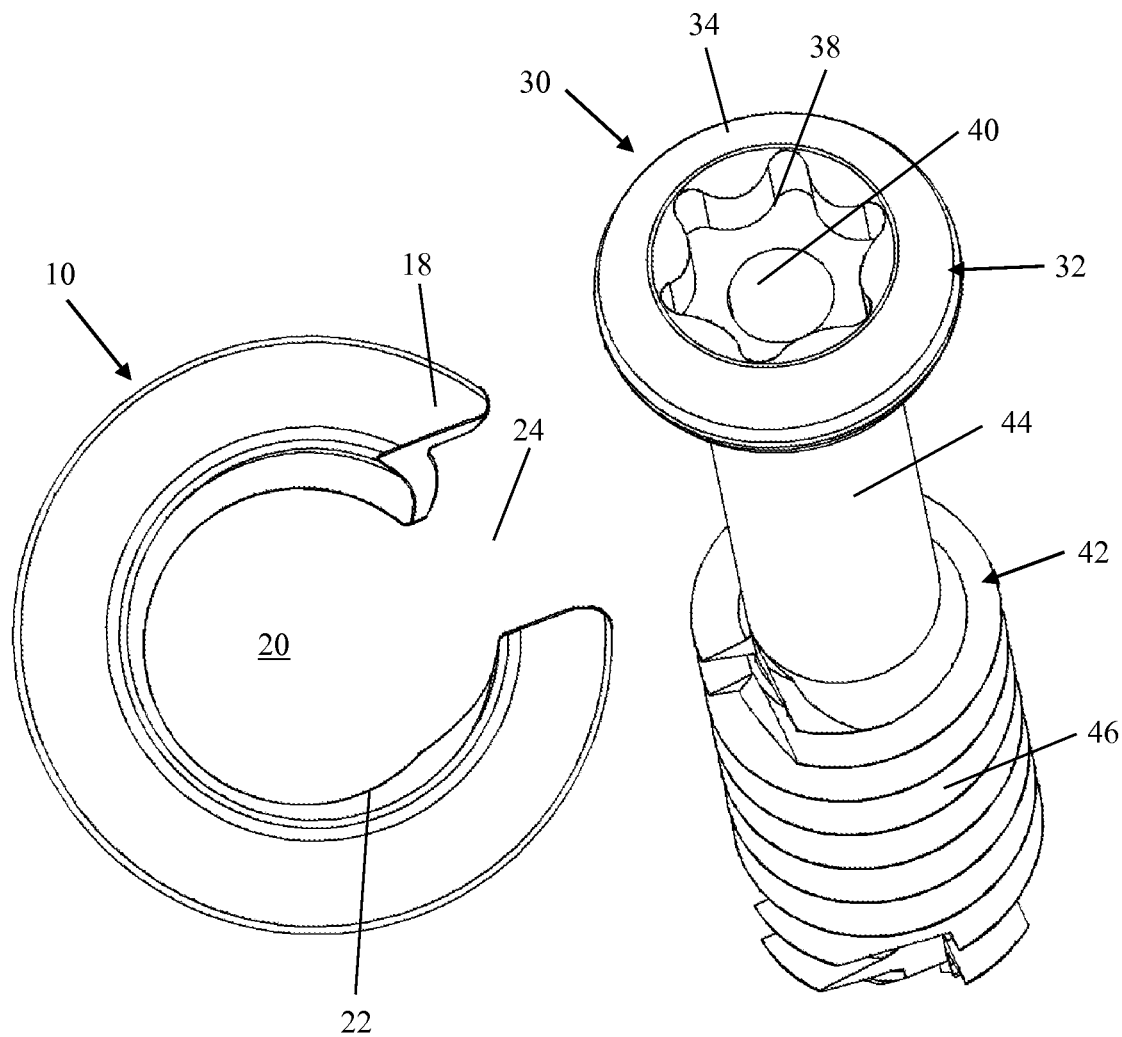
FIG. 6 is a top perspective view of the implant of FIG. 1 and a screw, in accordance with an aspect of the present invention.
Figure 7:
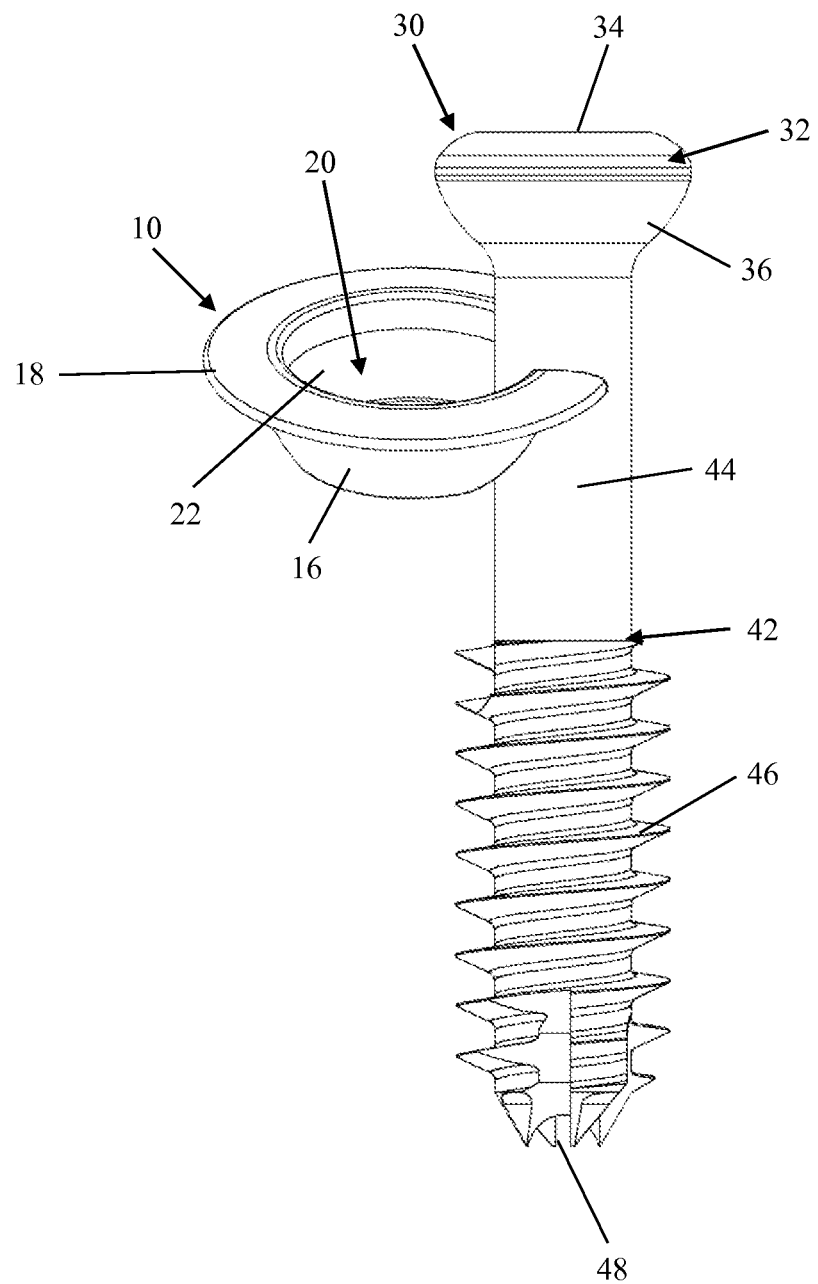
FIG. 7 is a side view of the implant of FIG. 1 being inserted onto a screw, in accordance with an aspect of the present invention.
Figure 8:
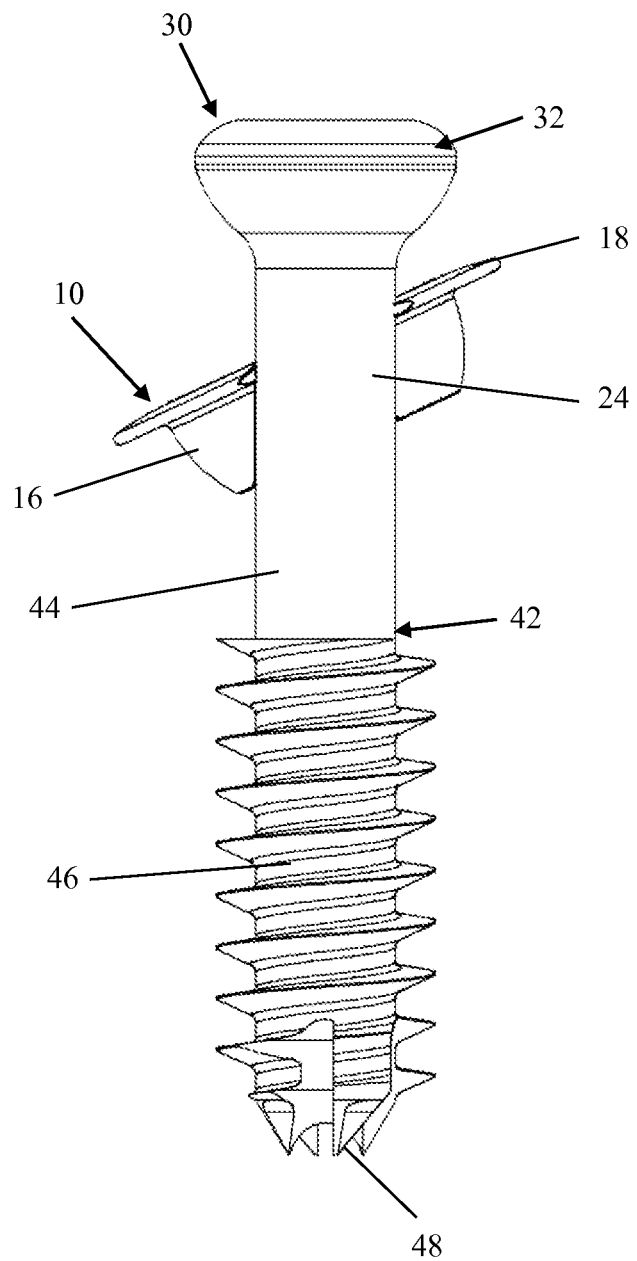
FIG. 8 is a front view of the implant of FIG. 10 with a screw being inserted, in accordance with an aspect of the present invention.
Figure 9:
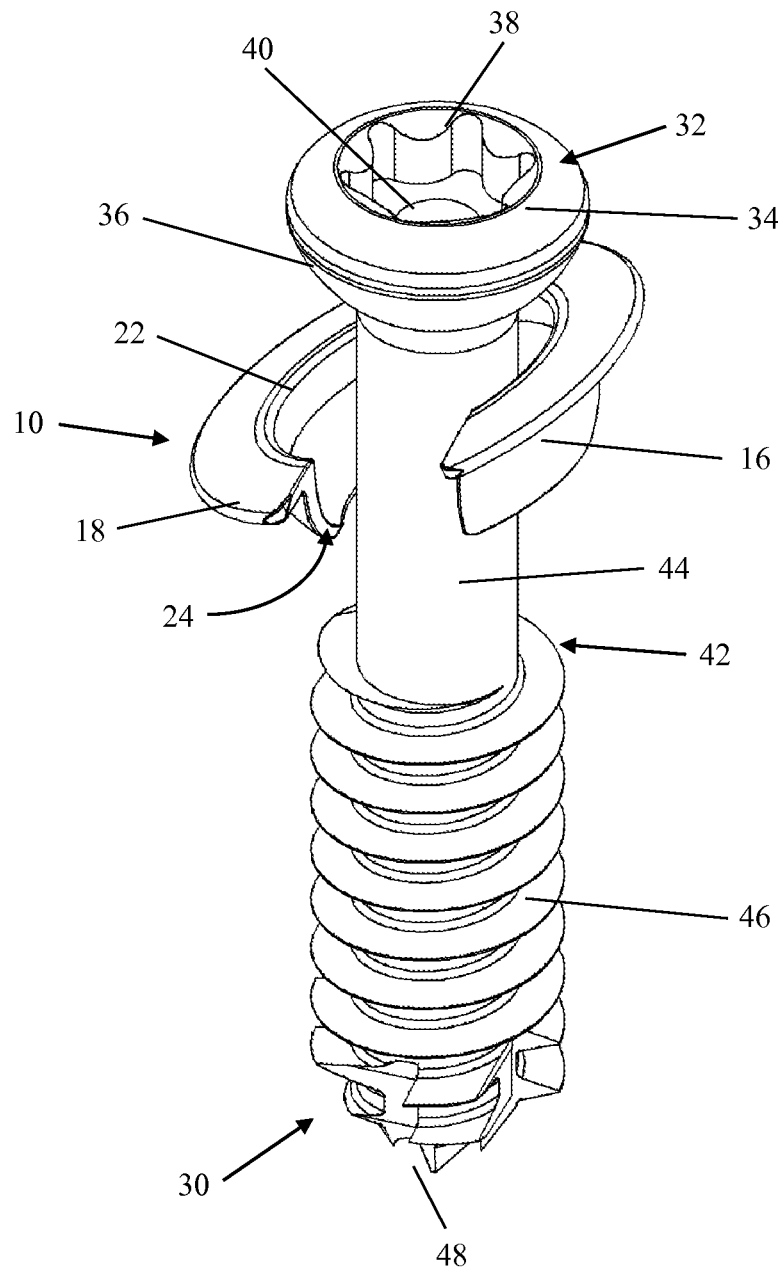
FIG. 9 is a perspective of the implant of FIG. 1 inserted onto a shaft of the screw, in accordance with an aspect of the present invention.

Referring now to FIGS. 6-13, a method for inserting the implants 10 onto a bone screw, fastener, or fixator 30 is depicted. The bone screw 30 may include a head portion 32 and a shaft portion 42, as shown in FIGS. 6-10. The head portion 32 may include a superior end 34 and an inferior end 36, as seen in FIGS. 7 and 10. The superior end 34 of the head portion 32 may have a tool engagement opening 38 and a center hole 40, as shown in FIGS. 6 and 9. The tool engagement opening 38 may have a multi-lobed shape as shown in FIGS. 6, 9, 11-12, although other polygonal shapes are also contemplated. As shown in FIGS. 11 and 12, the inferior end 36 may be configured to engage the interior surface 22 of the implants 10, respectively. The shaft portion 42 may include a smooth end 44 for engaging the implant 10 and a threaded end 46 for engaging a patient's bone, as seen in FIGS. 9-10. The threaded end 46 of the shaft portion 42 may include at least one sharp tip 48 to assist in insertion into the patient's bone.

Figure 13:
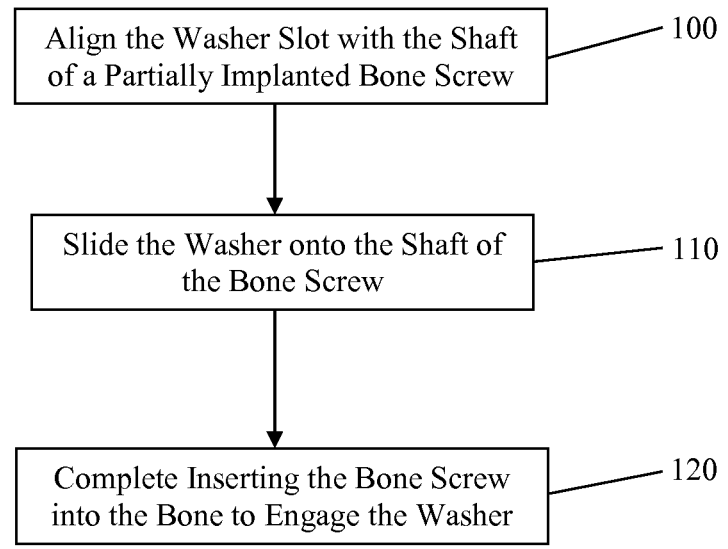
FIG. 13 depicts one embodiment of a surgical method for inserting an implant on a partially implanted bone screw, in accordance with an aspect of the present invention.

Referring now to FIG. 13, in order for the implant 10 to engage the screw 30, the screw 30 at least a portion of the smooth end 44 of the shaft portion 42 must be accessible by the surgeon. If the screw 30 has not been inserted into the patient, the shaft 42 of the screw 30 may be inserted through the central bore 20 of the implant 10 or the implant 10 may be inserted onto the smooth end 44 of the shaft 42 as described below with relation to insertion of the implant 10 onto partially inserted screws 10. If the implant 10 is being inserted into the patient after the bone screw 30 has already been fully implanted, the bone screw 30 will need to be backed out of the bone in order to expose a portion of the smooth end 44 of the shaft portion 42 for engagement with the implant 10. As shown in FIGS. 7 and 8, the slot 24 of the implant 10 may be aligned with the smooth end 44 of the shaft 42 of the screw 30 which is partially inserted into the patient's bone in step 100. The slot 24 of the implant 10 is aligned with the smooth end 44 of the screw 30 so that the face of the implant 10 is angled, the implant 10 may be pressed or slid onto the screw 30 to engage the smooth end 44 of the shaft portion 42 with the central bore 20 of the implant 10 and then turned to lock the implant 10 onto the screw 30 during step 110, as seen in FIGS. 9 and 10. The screw 30 may then be fully inserted into the patient's bone. As the screw 30 is screwed into the patient's bone, the inferior end 36 of the head portion 32 of the screw 30 is configured to engage the interior surface 22 of the implant 10 during step 120, as shown in FIG. 11. In addition, the exterior surface 16 and rim 18 of the implant 10 may engage the bone surface (not shown). As shown in FIG. 12 if the screw 30 is inserted into a bone on an angle the implant 10 is configured to still engage the inferior end 36 of the head portion 32 of the screw 30.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An implant for use with a bone fastener with a head portion and a shaft portion extending from the head portion along an axis of the bone fastener, comprising:
   an annular body portion extending from a top end to a bottom end, comprising:
   an exterior surface; and
   an annular interior surface extending from the top end to the bottom end defining a central bore extending from the top end to the bottom end along a central axis;
   a rim portion extending radially outwardly from the body portion at the top end; and
   a slot extending entirely through a section of the rim portion and the body portion such that the slot is in communication with the central bore,
   wherein the exterior surface extends from the bottom end to the rim portion, the exterior surface being convex in a direction extending along the central axis between the bottom end and the rim portion,
   wherein the interior surface of the body portion comprises a first interior surface portion extending from the top end toward the bottom end that is planar in a direction transverse to the central axis, and a second interior surface portion extending from the bottom end to the first interior surface portion that is concave in a direction extending along the central axis,
   wherein the slot extends along a slot axis that is angled with respect to the central axis, and
   wherein a width of the slot extending perpendicular to the slot axis is equal to or greater than a width of the shaft portion of the bone fastener extending perpendicular to the axis of the bone fastener.

2. The implant of claim 1, wherein the inner surface of the body portion includes a first inner diameter at the top end and a second inner diameter at the bottom end, the first inner diameter being larger than the second inner diameter.

3. The implant of claim 1, wherein the interior surface is configured to engage a head of a bone fastener.

4. The implant of claim 1, wherein the exterior surface is tapered from the top end to the bottom end.

5. The implant of claim 1, wherein the rim portion is configured to engage a bone surface.

6. The implant of claim 1, wherein the central bore is configured to engage a top portion of a bone fastener.

7. The implant of claim 6, wherein the shaft portion of the bone fastener comprises a smooth end and a threaded end, wherein the smooth end of the shaft portion is integral with the head portion.

8. The implant of claim 7, wherein the slot and the central bore are configured to receive the smooth end of the shaft portion therethrough.

9. The implant of claim 7, wherein an inferior end of the head portion bears against the interior surface of the body portion.

10. The implant of claim 1, wherein the slot axis is angled between 20 to 30 degrees relative to the central axis.

11. The implant of claim 10, wherein the slot is offset from the central axis between 0.3 mm and 1.6 mm.

12. The implant of claim 1, wherein the head portion of the bone fastener slidingly engages the concave first interior surface portion of the interior surface.

13. The implant of claim 1, wherein the exterior surface of the body portion is arcuately convex in a direction extending along the central axis between the bottom end and the rim portion.

14. The implant of claim 1, wherein the second interior surface portion of the body portion is arcuately concave in a direction extending along the central axis.

15. The implant of claim 1, wherein the top end of the body portion defines a top boundary of the implant.

16. The implant of claim 1, wherein a top surface of the rim portion extends downwardly toward the bottom end of the body portion as it extends radially outwardly from the top end of the body portion.

17. The implant of claim 1, wherein opposing sides defining the slot extend partially about the central axis as the opposing sides extend from the top end to the bottom end along the slot axis.

18. The implant of claim 1, wherein opposing sides defining the slot are planar and parallel to each other, as the opposing sides extend from the top end to the bottom end.

* * * * *